United States Patent [19]
Ornato et al.

[11] Patent Number: 4,457,312
[45] Date of Patent: Jul. 3, 1984

[54] METHOD AND APPARATUS FOR PROVIDING RECORDS OF EVENTS DURING A CARDIAC ARREST

[75] Inventors: Joseph P. Ornato; Larry Fennigkoh and Colleen S. Jaeger, all of Omaha, Nebr.

[73] Assignee: The Board of Regents of the University of Nebraska, Lincoln, Nebr.

[21] Appl. No.: 362,905

[22] Filed: Mar. 29, 1982

Related U.S. Application Data

[63] Continuation-in-part of Ser. No. 132,374, Mar. 21, 1980, abandoned.

[51] Int. Cl.³ .............................................. A61B 5/04
[52] U.S. Cl. .................................... 128/711; 33/1 C; 346/17; 346/33 ME
[58] Field of Search ............... 128/696, 710, 709, 711; 346/17, 33 ME, 62; 360/27; 33/1 C

[56] References Cited

U.S. PATENT DOCUMENTS

| | | | |
|---|---|---|---|
| 2,768,050 | 10/1956 | Alden | 346/103 |
| 3,041,415 | 6/1962 | Gratian | 360/27 |
| 3,087,488 | 4/1963 | Streimer | 346/33 ME |
| 3,380,064 | 4/1968 | Norris et al. | 346/17 |
| 3,434,149 | 3/1969 | Brousseau et al. | 346/17 |
| 3,653,058 | 3/1972 | Sundberg | 346/17 |
| 4,023,276 | 5/1977 | Furukawai et al. | 128/696 |

Primary Examiner—William E. Kamm
Attorney, Agent, or Firm—Vincent L. Carney

[57] ABSTRACT

To provide accurate reconstructable records of the events and therapy administered during a cardiac arrest, flow sheets are attached to the top of a timing clipboard. Each row of the flow sheet matrix indicates a different event and the columns indicate the time of events. The clipboard illuminates columns at intervals in the range of fifteen seconds to five minutes in a timed sequence across the flow sheet by energizing electroluminescent trips underneath the flow sheet to permit the nurse to indicate the events in the column corresponding to the time of the event. Other sensed data is recorded on a tape with timing signals for later reconstruction. When all of the columns have been covered, an alarm is sounded so that a new flow sheet may be attached. The page of the flow sheet is indicated on the clipboard for translation onto the flow sheet.

22 Claims, 8 Drawing Figures

EMERGENCY DEPARTMENT CARDIAC ARREST FLOWSHEET

20

CLASS _____ 22

NAME _____ 24

LOCATION _____ 26

| | Page | 1 | | 2 | 3 | | 4 | 5 | | 6 | 7 | | 8 | 9 | 10 | |
|---|---|---|---|---|---|---|---|---|---|---|---|---|---|---|---|---|

START TIME _____
RHYTHM:
    VF _____
    VT _____
    ASYS _____
    IVR _____
    SVR _____
    _____
    _____
    _____

DEFIBRILLATION 400WSEC:
           WSEC:
INTUBATION E.T. _____
        E.O.A. _____
THUMPER
IV:   SITE   SOLN
  1. _____ _____
  2. _____ _____
  3. _____ _____

MEDS:
  Sodium Bicarbonate ___
  Epinephrine _____
  Lidocaine _____
  Atropine _____
  Calcium _____
  Isuprel _____
  _____
  _____

ARTERIAL BLOOD GASES:
N-G TUBE: _____
PACEMAKER: _____
PULSE: _____
BP: _____
UH

28

METHOD AND APPARATUS FOR PROVIDING RECORDS OF EVENTS DURING A CARDIAC ARREST

REFERENCE TO RELATED APPLICATIONS

This application is a continuation-in-part application of U.S. application Ser. No. 132,374 for TIMING CLIPBOARD filed by Joseph P. Ornato et al on Mar. 21, 1980 and now abandoned and assigned to the same assignee as this application.

BACKGROUND OF THE INVENTION

This invention relates to timing clipboards which provide information and indicate where information is to be entered on flow sheets in a synchronized manner.

During certain emergency procedures such as during cardiac arrest, the time of occurrence of events and an identification of events are recorded for later correlation with electrocardiograms to reconstruct what happened during the emergency procedure. In the prior art, the recording of the events and their time is done manually by a nurse jotting down the events and the time for later coordination with the electrocardiograms.

The prior art method of recording events and time for later correlation with other information such as electrocardiograms is not entirely satisfactory. The entries are frequently inaccurate and the correlation is difficult to make.

SUMMARY OF THE INVENTION

Accordingly, it is an object of the invention to provide a novel method for recording a series of events.

It is a further object of the invention to provide a novel apparatus which aids in recording a series of events.

It is a still further object of the invention to provide a timing clipboard which may be used to time the entry of information with a series of events.

It is a still further object of the invention to provide a method and apparatus for recording information during emergency medical procedures.

In accordance with the above and further objects of the invention, flow sheets are used to record information. Sections of the flow sheet having an area of at least 0.5 square centimeters are sequentially indicated at intervals in the range of 15 seconds to 5 minutes to guide the recording of the information in a predetermined pattern which may be correlated by signals to a series of events. For example, a flow sheet has events identified in a column, with each event in the column identifying a different row. Successive locations in the rows are provided for indicating the time of the event.

The locations for indicating each time for the time rows of events form columns so that a check in a location of a row indicates the time of the event. Each column may, for example, indicate one minute in a sequence of twenty minutes. The timing signals used to indicate the columns may be applied to another medium for recording to correlate information recorded on the medium with the flow sheets. The apparatus provides other external information such as audibly indicating when a flow sheet should be changed.

Advantageously, the columns of the flow sheet are illuminated by electroluminescent strips which are sequentially energized in one minute intervals. Thus the nurse may make entries in the illuminated column, opposite the events such as by a check mark or the like to simplify the procedure. One application for this equipment is for the manual entry of cardiac arrest events by a nurse in a manner that permits later correlation with electrocardiographic signals recorded on magnetic tape with timing signals. In such an application, the sections should have an area of at least 0.5 square centimeters to provide adequate space for indicating parts of this area for specific events in a cardiac arrest situation. Where the area is shaped as a column, the column should be at least 3 inches long.

The measured signals have characteristics that change in accordance with circumstances. For example the cardiographic signals may change with certain medication. The time interval between such changes is relatively long and much greater than the frequency of the measured signals.

The interval between indications of columns in response to timing signals is selected to be shorter than the intervals between such changes and longer than the frequency of the measured signals.

Illuminated clipboards are known. However, these known clipboards do not permit the easy manual recording of information in sections that are automatically indicated in a pattern for later correlation with other recorded data.

From the above summary, it can be understood that this method has the advantages of permitting easy and quick recording of events and their time and their correlation with other automatically recorded information. The timing clipboard which is used in practicing the inventive method has the further advantages of being light, easy to handle and economical in construction.

SUMMARY OF THE DRAWINGS

The above noted and other features of the invention will be better understood from the following detailed description when considered with reference to the accompanying drawings in which:

FIG. 2 is a plan view of a portion of the embodiment of FIG. 1;

DETAILED DESCRIPTION

Figure 1:
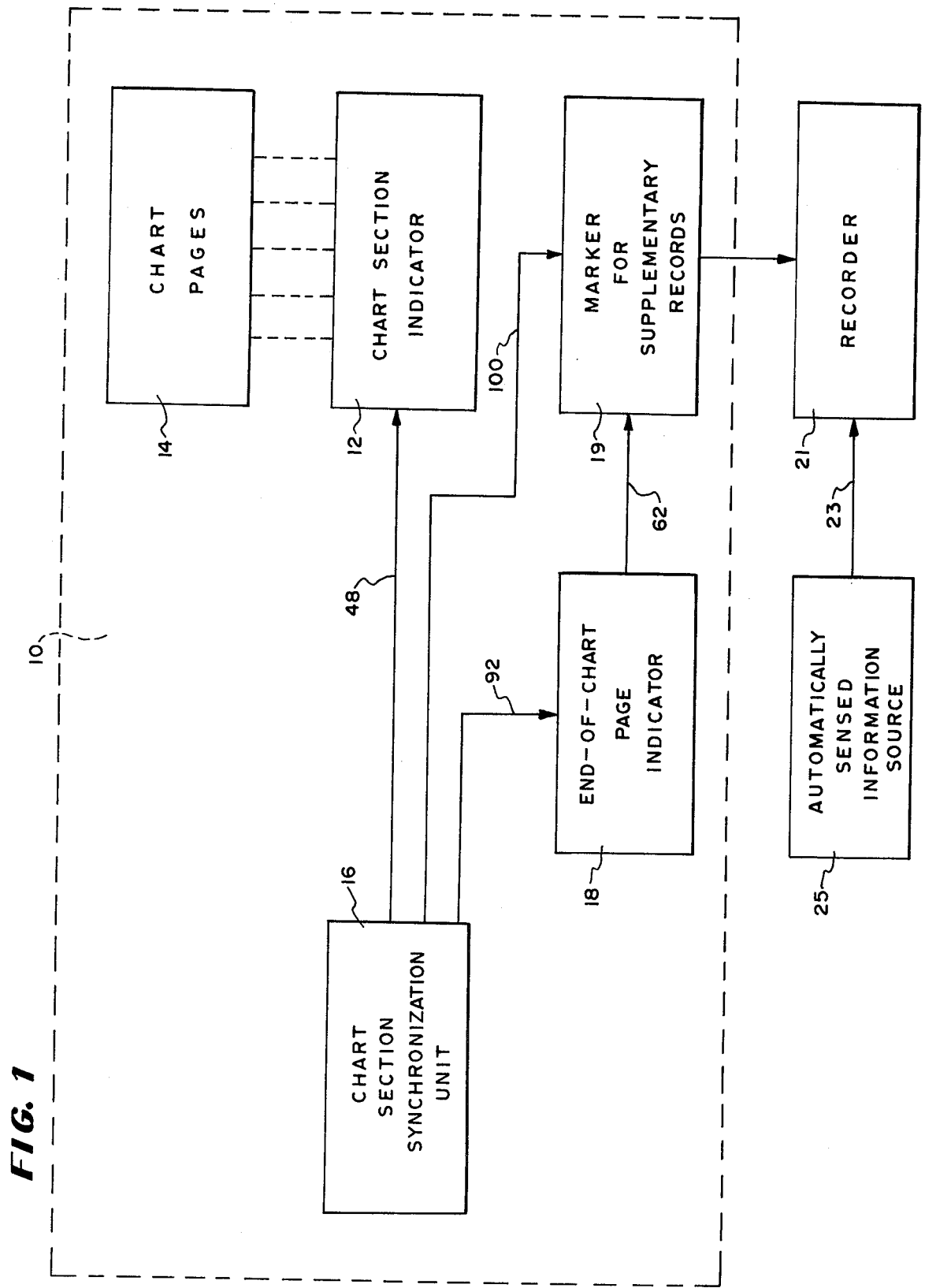
FIG. 1 is a block diagram of the timing clipboard connected to a recorder for correlation of entries with other recorded information from an automatically-sensed-information source in accordance with an embodiment of the invention.

In FIG. 1, there is shown a block diagram of a timing clipboard 10 electrically connected to a recorder 21, which is electrically connected to an automatically sensed information source 25 to receive information to be coordinated in time with entries made using the timing clipboard 10. The timing clipboard 10 has as its principal parts a chart section indicator 12, chart pages 14, a chart section synchronization unit 16, an end-of-chart page indicator 18 and a marker for supplementary records 19.

The chart section indicator 12 is adapted to receive the chart pages 14 on its surface and is controlled by the chart section synchronization unit 16 to which it is electrically connected. The chart section synchronization unit 16 is also electrically connected to the end-of-chart page indicator 18 and to the marker for supplementary records 19.

To synchronize the indications on the chart pages 14 with other records such as electrocardiograms recorded by the recorder 21, the marker for supplementary records 19 is a signal generator electrically connected to the chart section synchronization unit 16 and to the end-of-chart page indicator 18. It applies timing signals to the recorder 21 which indicate the time on the electrocardiograms that are recorded by the recorder 21 in response to signals from the electrodes attached to the patient indicated generally in FIG. 1 by the automatically sensed information source 25. The recording timing signals correspond to the times that the columns are illuminated for marking and thus provide a ready correlation between the electrocardiogram and the flow sheets on the chart pages 14.

While in the preferred embodiment the recorder is a magnetic tape recorder and the maker generates a signal tone to be recorded on the tape, other types of recorders and markers can be used. For example, if a strip chart recorder is used, the marker for supplementary records 19 may be a pen marker. Such a pen marker may be digital or analog and may record a sequence of numbers or simply indicate the time and the page in sequence.

In the preferred embodiment, the recorder 21 records the electrocardiogram on tape as it is generated. After recording, the flow sheet can be compared with the EKG rhythm strips generated from the Holter tape. The magnetic recording, since it is entirely in sequence, can readily be correlated with the pages and columns either by the superposition of signals from the marker for supplementary records 19 or by an audible sound or signal on the tape recorder.

Before using the timing clipboard 10 at least one chart page 14 is positioned on top of the chart section indicator 12. In operation, the chart section indicator 12 indicates different sections on the chart page attached to it in a predetermined pattern in accordance with signals received from the chart section synchronization unit 16 to designate to the user a portion where information is to be entered on the chart page or information is to be read at a specified time. The synchronization of changes of pages or other information not directly on the chart is provided by the end-of-chart page indicator 18 in synchronization with the information from the chart section synchronization unit 16. The timing information is also applied to the recorder 21 to later enable coordination of the information on the chart pages 14 with the signals from the automatically sensed information source 25.

The chart pages 14 are flow sheets which require entries to be made or instructions to be followed in some fixed pattern. This pattern may occur in timed increments of equal duration or in coordination with another event or timed in accordance with some other pattern. The chart section indicator 12 indicates the particular area at the right time so that entries may be made or information read at that time. Since the time section pattern is known, the time sequence of data recorded in accordance with this pattern may be reconstructed later from the sections on which it was recorded on the chart pages 14.

Other information not on the chart pages 14 is provided by another unit which in the preferred embodiment is an end-of-chart page indicator 18. In the preferred embodiment this unit indicates when the chart is to be changed and a new chart positioned on the chart section indicator 12 to continue the record.

In FIG. 2, there is shown one type of chart page 14 used particularly for emergency department cardiac arrest procedures. This flow sheet is designed to be attached to the clipboard by clips as will be explained hereinafter and has entries printed on it such as a title 20, labeled spaces for indicating the class of patient 22, the name or other identification of the patient 24, and the location 26.

The flow chart itself includes a column 28 which identifies rows on the flow sheet in which entries are to be made and contains other spaces for information such as start time and page number. The rows are identified by type of data such as rhythm, defibrillation, intubation, thumper, medication, and arterial blood gases. The rows are intended for individual marking in a timed sequence which runs from left to right. Numbers are provided to be circled for the pages.

In the preferred embodiment, the particular columns in which entries are to be made opposite the selected designations for the row are illuminated by the chart section indicator 12 (FIG. 1) although other techniques may be used for indicating the particular column. While the pattern for this embodiment is sequential from left to right, other patterns may be used such as interleaved patterns of columns right to left or a sequence of entire block sections or the like. The time periods for each column are the same in the preferred embodiment for emergency department cardiac arrest but may differ in other embodiments.

In this embodiment the columns which are indicated at 30 on the chart, are boxes which form a matrix together with the indicated lines for the labeling on the lefthand side. The columns are approximately 8¼ inches long and divided into four sections by three ¼ inch long spaces. They include 30 spaces, each being ¼ inches long to indicate events. For efficient use the columns should be at least 3 inches long. Of course, instead of labels on the chart itself, specialized clipboards may be used which include the particular labels for sections and the chart only includes information to be viewed at a certain time and places for data to be recorded.

This flow chart illustrates the usefulness of the electronic clipboard. It solves a major long standing problem. The problem is retrospectively analyzing the events and therapy administered during a cardiac arrest to obtain a better understanding of what drugs should be used and when they should be used. To reconstruct the procedures, well-documented flow sheets are necessary. In the conventional prior art systems, nurses jotted down the events taking place during a cardiac arrest and recorded the time of occurrence next to each data entry. Strips of the electrocardiogram monitoring during the cardiac arrest were similarly collected with the time of occurrence written on the EKG strip.

With the prior art system, at the end of the cardiac arrest, the nurse and physician were left with pieces of paper containing numerous entries and times and a stack of EKG rhythm strips. Invariably, key rhythm strips or entries on the record were omitted or the times were inaccurate.

In operation, at the beginning of the cardiac arrest, the recording nurse turns on the clipboard and records the start time at the top of the flow sheet. The vertical column of boxes is automatically illuminated from below the page in the preferred embodiment by lamps within the clipboard (described hereinafter) and remains on during the first minute. During this time, the nurse places a check mark in the boxes applicable to what is being done. For example, if the patient is intubated and defibrillated, these boxes are checked.

At the beginning of the second minute, the second column of boxes is automatically illuminated and the first one is extinguished. The sequence is continued with one minute intervals between each change. When the last column of boxes on the page is completed, the device automatically resets the first column and an audible alarm sounds to notify the nurse that a new flow sheet should be placed on the clipboard. The page number of the flow is indicated by a lamp, which in the preferred embodiment is an electroluminescent lamp, on the panel and is marked on the flow sheet by the nurse.

As the flow sheet is being marked by the operator, the recorder 21 records the electrocardiogram. Later, the magnetic tape from the recorder 21 is used to prepare EKG strips and the flow sheet is compared with the EKG strips generated from the Holter tape. The magnetic recording, since it is entirely in sequence, provides an easy correlation with the pages and columns. Moreover, this process is aided by the superposition of signals from the marker for supplementary records 19 (FIG. 1) or by an audible sound or signal on the tape recorder.

Although one minute intervals have proved satisfactory in the preferred embodiment other time periods may be used. The intervals between the leading edge of timing signals should have a duration within the range of fifteen seconds and five minutes. The sensed data has a frequency, with at least one characteristic which may change under some circumstances at unpredictable time periods which are greater than the period of said frequency of the sensed data but less than the intervals between said timing signals.

Figure 3:
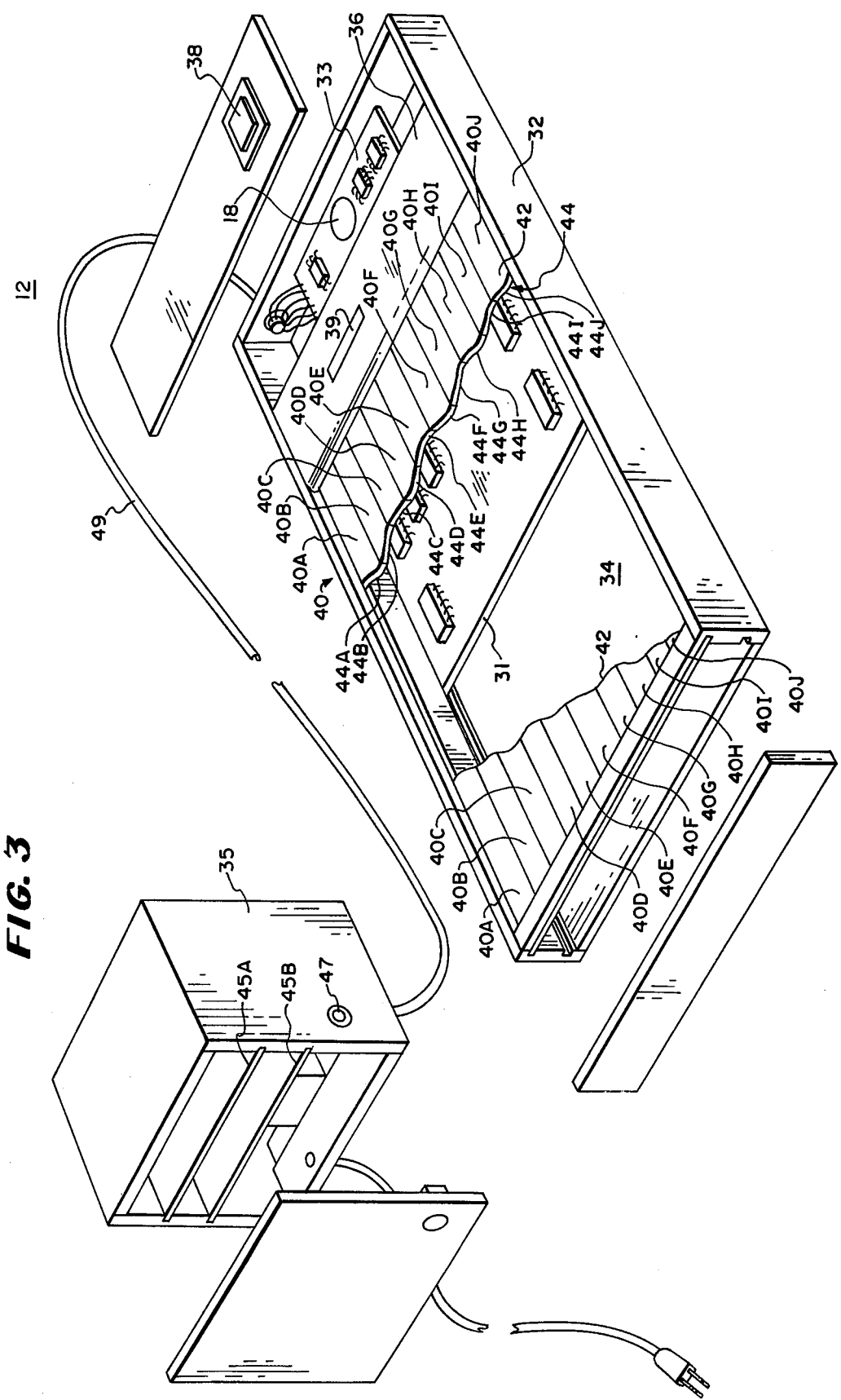
FIG. 3 is a fragmentary, exploded, simplified perspective view partly broken away of a portion of the embodiment of FIG. 1.

In FIG. 3, there is shown a fragmentary, simplified, exploded perspective view of the chart section indicator 12 having a housing section 32, an electroluminescent section 34 and a power supply section 35.

The electroluminescent section 34 includes a spring biased plastic clip 36 for holding the chart pages 14 (FIGS. 1 and 2) in place, a power on-off switch 38, a page indicating section 39, a top transparent conductor section 40, a base support 42, and a bottom conductor section 44. The top and bottom conductor sections 40 and 44 each include a plurality of conductive strips 40A-40J and 44A-44J respectively with electroluminescent material between then and are each insulated from the other.

Corresponding pairs of the conductors are connected as explained hereinafter to be energized by an alternating potential and are aligned with the columns of the chart pages 14 (FIGS. 1 and 2) in a predetermined sequence to form a line of light beneath the columns of chart pages. The clip 36 holds the chart pages in place.

To successively energize the conductors in the sections 40 and 44, the end-of-chart page indicator 18, the chart section synchronization unit 16, and the marker for supplementary records 19 (FIG. 1) are mounted within the housing section 32 and include circuitry to be explained in greater detail hereinafter. The circuitry is mounted on circuit boards two of which are shown at 31 and 33 within the housing section 32 for convenience.

The power supply section 35 similarly includes an outlet plug 47 and circuit boards two of which are shown at 45A and 45B for mounting the necessary circuits. The power for operating the circuits in the housing section 32 is supplied through a cable 49 and the timing signals are transmitted through the cable 49 from the housing section 32 to the outlet plug 47 in the power supply section 35 for connection to the recorder 21 (FIG. 1).

In operation, with the chart pages 14 (FIG. 1) held by the clip 36, successive pairs of oppositely disposed aligned conductors 40A-40J and 44A-44J are energized to excite the electroluminescent material between them. The chart pages 14 are positioned by the clip 36 so that each pair of conductors is aligned with one of the columns 30 (FIG. 2) to illuminate that column through the transclucent paper. Successive pairs of the conductors are energized in one minute intervals.

When all of the ten columns have been illuminated, the audible end-of-chart page indicator 18 is energized, the page indicating section 39 indicates the next page and the nurse changes the chart page and marks the page number on the new page. The sequence repeats. In the meantime, the nurse is making the proper entries in the columns and the timing signals indicating the page and the column are being recorded on magnetic tape in the recorder 21 by the marker for supplementary records 19 as the electrocardiogram signals are received on conductor 23 from the electrocardiogram for recording in the recorder 21 to provide a permanent correlation between the information on the chart pages 14 and the electrocardiogram signals (FIG. 1).

Figure 4:
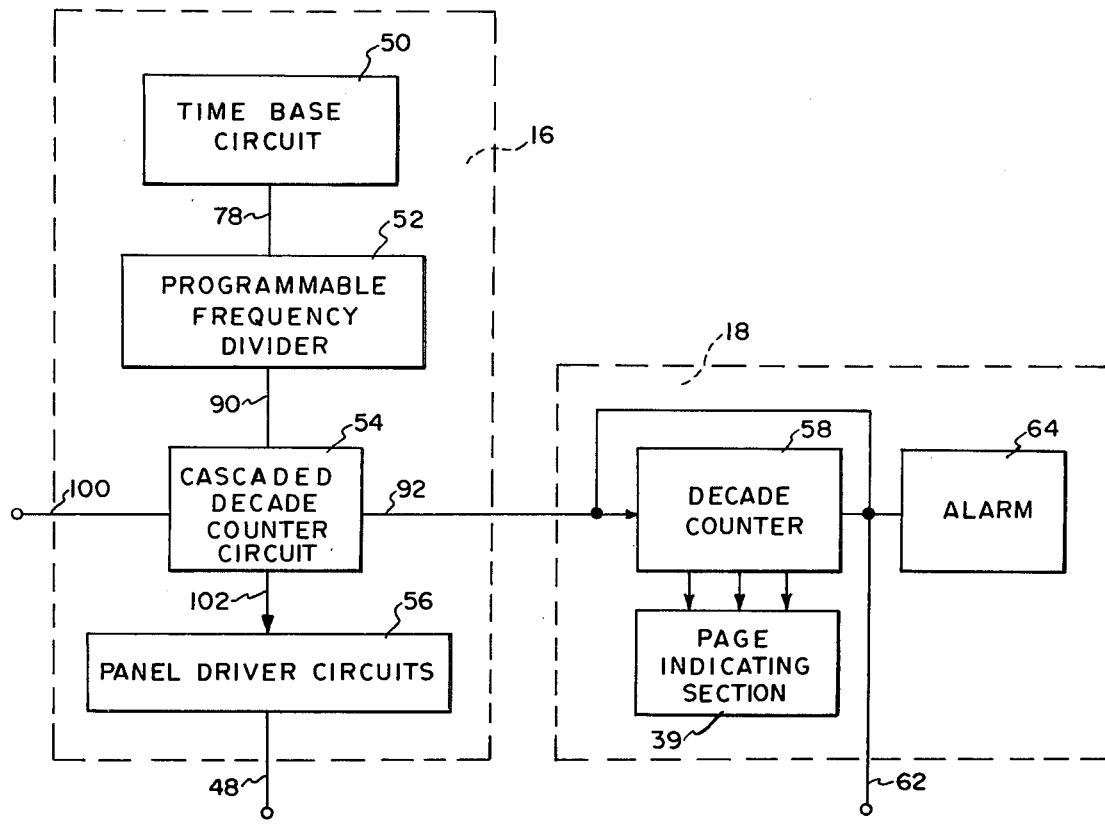
FIG. 4 is a block diagram of a portion of the embodiment of FIG. 1.

In FIG. 4, there is shown a block diagram of the chart section synchronization unit 16 and the end-of-chart page indicator 18 connected together to apply signals through conductor 48 to the chart section indicator 12 (FIG. 1), through conductor 100 to the marker for supplementary records 19 (FIG. 1), and through conductor 92 to the end-of-chart page indicator 18.

To generate timing signals, the chart section synchronization unit 16 includes a time base circuit 50, a programmable frequency divider 52, a cascaded decade counter circuit 54, and a panel driver circuit 56. The time base circuit 50 generates 60 Hz pulses and applies them to the programmable frequency divider 52, which in turn applies them to the cascaded decade counter circuit 54 after dividing them into one minute intervals. The cascaded decade counter circuit 54: (1) applies the pulses to the panel driver circuits 56 through a plurality of conductors indicated at 102 in FIG. 4 and shown as 102A-102C in FIG. 6 below; and (2) divides the pulses further into twenty minute intervals for application to the end-of-chart page indicator 18 (FIG. 1) through conductor 92.

The pulses applied to the end-of-chart page indicator 18 are used to indicate the page in a manner to be described hereinafter and the pulses applied to the panel driver circuits 56 initiate the sequence of one minute steps which illuminate the sections of the chart section indicator 12 (FIGS. 1 and 2). The panel driver circuits 56 applies these pulses through a plurality of conductors shown at 48 in FIG. 4 to the chart section indicator 12, to the marker for supplementary records 19 for use in connection with the electrocardiogram recording.

To provide end-of-page signals, the end-of-chart page indicator 18 includes a decade counter 58, an audible alarm device 64 and a page indicating section 39. Conductor 92 transmits signals to the decade counter 58, through conductor 62 to the marker for supplementary records 19 (FIG. 1) and to the alarm device 64 to indicate to the nurse that it is necessary to change charts. The decade counter 58 energizes lamps indicating the page at each count it receives.

In operation, the time base circuit 50 provides pulses to the programmable frequency divider 52 which divides those pulses down to the time period desired to illuminate successive sections of the chart section indicator 12 (FIG. 1). These pulses are applied to the cascaded decade counter circuit 54 which decodes the pulses to select the appropriate section of the chart section indicator 12. In the preferred embodiment this is accomplished by applying the pulses one after the other in series through individual drivers within the panel driver circuits 56, each of which energizes in succession a different pair of conductors 40A–40J and 44A–44J to illuminate a different column of the chart pages 14 (FIGS. 2 and 3).

To indicate the time for changing charts, the cascaded decade counter circuit 54 transmits pulses: (1) to the end-of-chart page indicator 18, where they trigger the alarm device 64; (2) to the decade counter 58 which counts them into the page indicating section 39 to indicate the page number; and (3) to the marker for supplementary records 19 (FIG. 1) through conductor 62.

Figure 5:
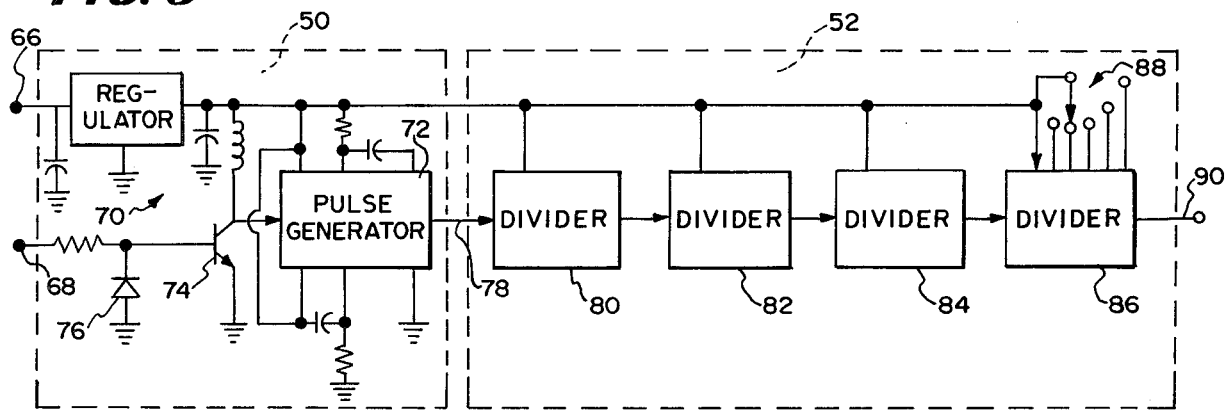
FIG. 5 is a schematic circuit diagram of a portion of the embodiment of FIG. 4.

In FIG. 5, there is shown a circuit diagram of the time base circuit 50 and the programmable frequency divider 52 electrically connected together to provide pulses to the cascaded decade counter circuit 54 (FIG. 4) through conductor 90. The time base circuit 50 receives a positive 5 volts on terminal 66 from conductor 48 and 60 Hz pulses on terminal 68 from a power supply. The 5 volt source is filtered and regulated by a 5 volt regulator in a conventional manner by the regulator filter circuit 70 and applied to the pulse generator 72. The 60 Hz pulses are applied to the pulse generator 72 through an NPN transistor 74, with the negative peaks being shunted to ground through a diode 76 and the pulse generator 72 transmits pulses through a conductor 78 to the programmable frequency divider 52 in response.

The programmable frequency divider 52 includes first, second, third, and fourth dividers 80, 82, 84 and 86 and a selector switch 88 electrically connected to the programmable divider 86 for selecting the number by which it divides.

The divider 80 divides pulses on conductor 78 by ten and applies them to the divider 82 which divides them by six before applying them to the divider 84 which divides them by fifteen. The output from the divider 84 is applied to the divider 86 which divides them by a whole integer between one and fifteen depending on the setting of the selector switch 88. The output from the divider 86 and from the programmable frequency divider 52 is applied through a conductor 90 to the cascaded decade counter circuit 54 (FIG. 4).

Figure 6:
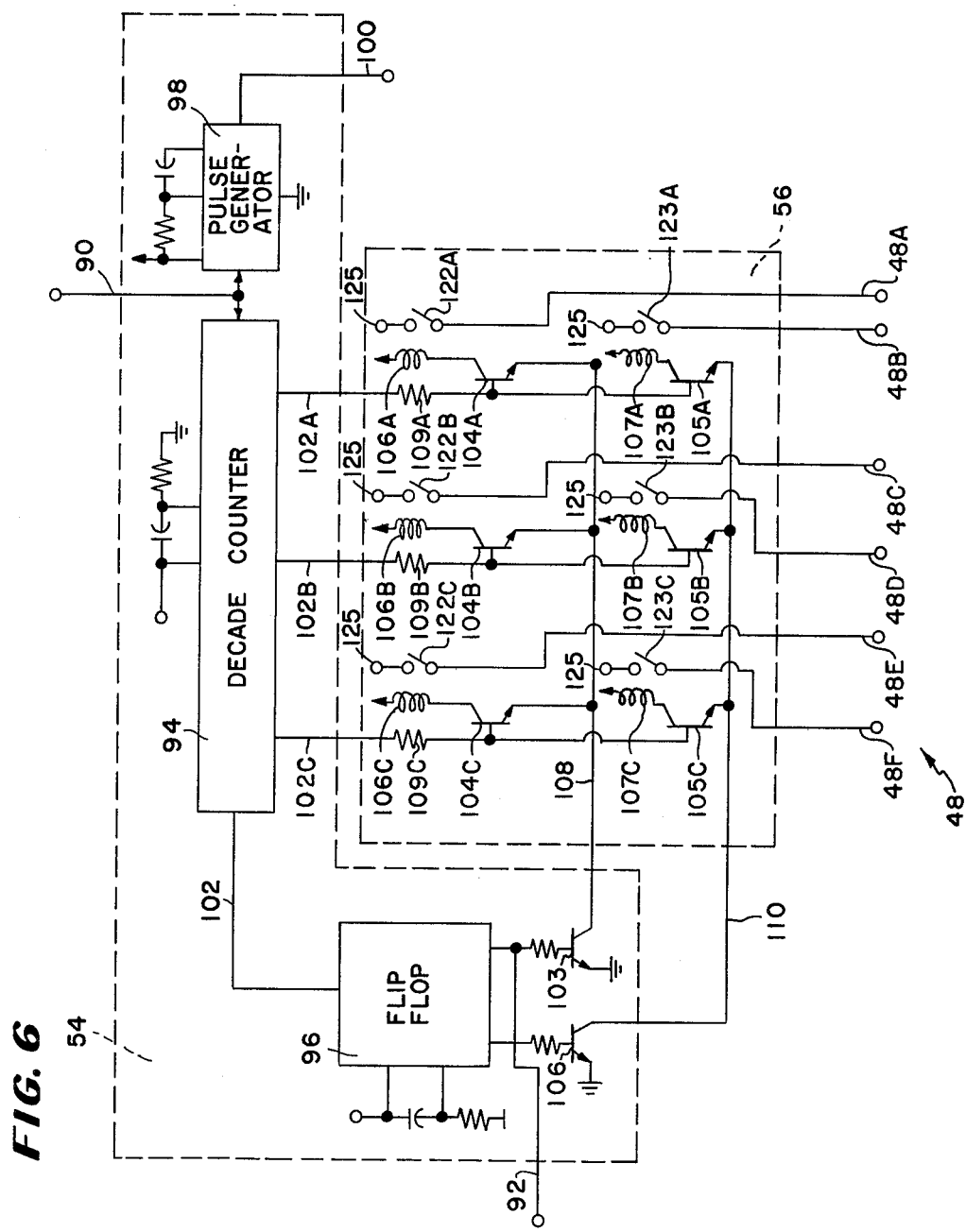
FIG. 6 is a schematic circuit diagram of another portion of the embodiment of FIG. 4.

In FIG. 6, there is shown a circuit diagram of the cascaded decade counter circuit 54 and the panel driver circuits 56 electrically connected to receive pulses on conductor 90 from the programmable frequency divider 52 and to provide pulses to the end-of-chart page indicator 18 through a conductor 92 and to the section indicator panel through conductors 48, six of which are shown at 48A–48F for illustration.

To provide a sequence of pulses, the cascaded decade counter circuit 54 includes a decade counter 94, a flip-flop 96 and a pulse generator 98. The pulse generator 98 and the decade counter 94 receive pulses through conductor 90 from the programmable frequency divider 52, with the pulse generator 98 shaping the pulses and providing them to conductor 100 for application to the marker for supplementary records 19 (FIG. 1).

The decade counter 94 counts the pulses across its ten stages and at each stage applies pulses to an output conductor, three stages being shown in FIG. 6 at 102A, 102B and 102C for simplicity although the preferred embodiment includes ten stages to provide for the successive illumination of ten columns on the chart pages 14 (FIGS. 1 and 2).

The last stage of the decade counter 94 is electrically connected to the input terminal of flip-flop 96 to switch it from one of its states to the other each time the decade counter 94 receives ten counts and is reset. The set output of the flip-flop 96 is electrically connected through a current limiting resistor to the base of the first transistor 103 and the reset output terminal of the flip-flop 96 is electrically connected to the base of a second transistor 106 through a current limiting resistor. The NPN transistors 103 and 106 have their emitters grounded and their collectors electrically connected through conductors 108 and 110, respectively to the panel driver circuits 56.

To cause pairs of conductors 40A–40J and 44A–44J (FIG. 3) to be energized by a source of a.c. power for illumination of columns of the chart pages 14 (FIGS. 1 and 2), the panel driver circuits 56 has: (1) the corresponding base of each of the NPN transistors 104A–104C, 105A–105C electrically connected through a corresponding current limiting resistance 109A–109C to corresponding ones of the outputs 102A–102C of the counter; (2) each of the emitters of transistor 104A–104C electrically connected to conductor 108 and each of the emitters of transistors 105A–105C electrically connected to conductor 110; and (3) their collectors connected to a source of positive 5 volts through the coil of a corresponding one of the relay switches 106A–106C and 107A–107C.

The coils 106A–106C and 107A–107C are positioned adjacent to corresponding ones of the contacts of reed relays 122A–122C and 123A–123C. One contact of each of the relays is electrically connected in an a.c. source 125 suitable for exciting the electroluminescent strips so that when any of the relay contacts are closed its corresponding conductors of the series 40A–40C, 44A–44C are energized to cause the corresponding electroluminescent strip between them to emit light (FIG. 3).

With this arrangement, the relay contacts 122A–122C are closed in sequence during a first count cycle of the decade counter 94 and relay contacts 123A–123C during a second count cycle since transistors 104A–104C are driven to conduction by flip-flop 96 during the first cycle and transistors 105A–105C during the second cycle. Since in the preferred embodiment decade counter 94 has ten stages, twenty columns are illuminated in sequence. Conductor 92 is energized once for each twenty counts under the control of the flip-flop 96 and the counter which together select the transistors 104A–104C and 105A–105C that are to conduct.

While only six sets of outputs for the counter, pairs of relays, transistors and conductors are disclosed for simplicity, it is to be understood that in the preferred embodiment twenty such sets are used to illuminate twenty columns. Moreover, any number of sets may be used to correspond with any selected particular number of sections of a chart page 14 (FIG. 1).

Figure 7:
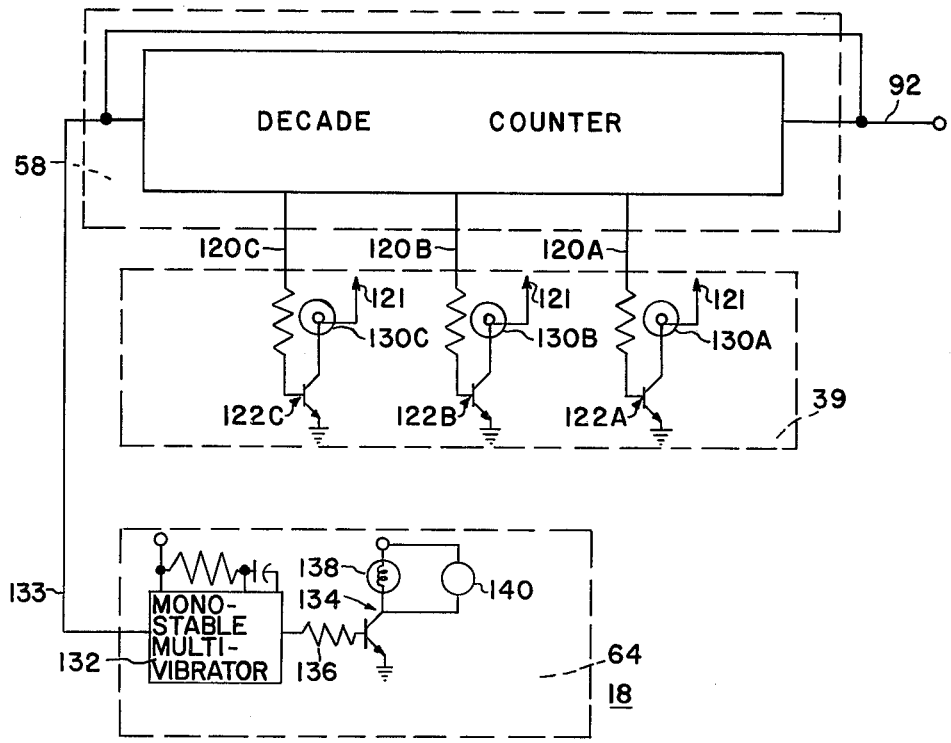
FIG. 7 is a schematic circuit diagram of still another portion of the embodiment of FIG. 4.

In FIG. 7, there is shown a schematic circuit diagram of the end-of-chart page indicator 18 having the decade counter 58, the page indicating section 39 and the alarm device 64. The decade counter 58 receives pulses from conductor 92 which is connected to one of the outputs of the flip-flop 96 (FIG. 6) to indicate each time that all twenty of the columns on a page have been illuminated. Conductor 92 is also connected directly to the audible alarm device 64.

The decade counter 58 includes ten outputs, three of which are shown at 120A, 120B and 120C. Each of the output terminals of the decade counter 58 is electrically connected to a corresponding one of the NPN transistors 122A–122C, each of which has its emitter grounded and its collector connected to a source of a positive 5 volts 121 through corresponding one of the reed relay coils, activation of which transfers power to a circular section 130A–130C of the electroluminescent panel to provide an indication of the page.

In operation, as the decade counter 58 moves one position in response to the flip-flop 96 (FIG. 6) changing state, a different one of the electroluminescent panels 130A–130C is illuminated to indicate a different page which can then be marked.

Each time a pulse is applied to the decade counter 58, it is also applied to the conductor 133 which transmits it to the monostable multivibrator 132. The monostable multivibrator 132 applies this pulse to the audible alarm circuit 134 while it is preset for a period of time set by the time constant of the multivibrator.

The audible alarm circuit 134 includes transistor 136, audible alarm 140 and lamp 138. The output of the monostable multivibrator 132 is connected to the base of the transistor 136, the emitter of which is grounded and the collector of which is connected to a source of positive potential through the lamp 138 and to an audible alarm 140 so that an audible alarm is provided and a lamp illuminated to indicate to the nurse that the page should be changed.

In operation, the end of page signals are applied by the flip-flop 96 (FIG. 6) through conductor 92 to the decade counter 58. As the decade counter 58 counts one position, it energizes a different one of the driver circuits 122A–122C which in turn illuminates a different one of the electroluminescent lamps 130A–130C indicating the page on the clipboard.

The electroluminescent panels are located across the top of the clipboard 12 as shown in FIG. 3 so that the nurse may readily note the page and circle the appropriate number on the chart pages 14 (FIG. 2). Each pulse applied by conductor 92 is also applied to the monostable multivibrator 132 which provides an output pulse that enables current to flow from a 5 volt source through the lamp 138 and the alarm 140, thus directing the attention of the nurse to the need to change the page.

Figure 8:
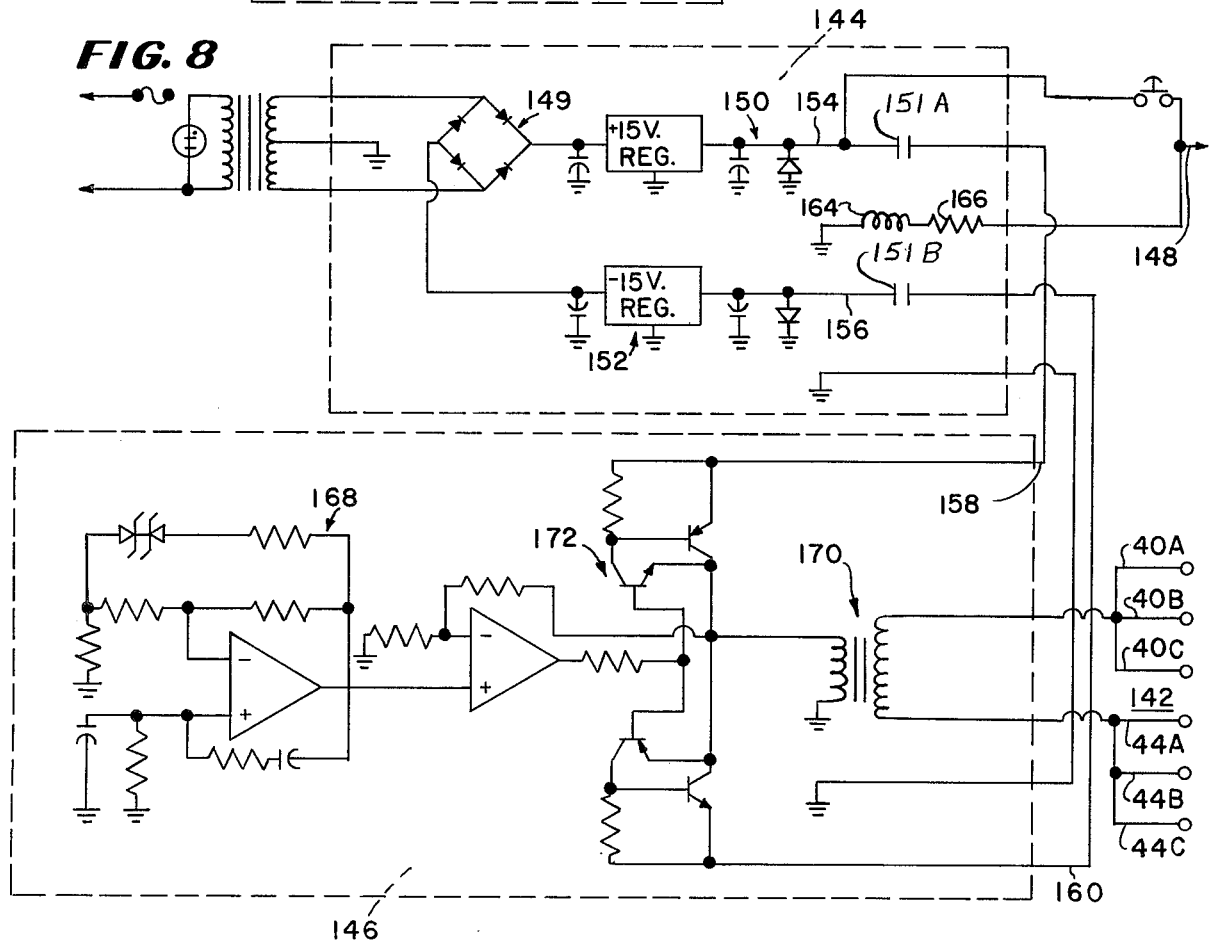
FIG. 8 is a schematic circuit diagram of a power supply useful with the embodiment of FIG. 1.

In FIG. 8, there is shown a power supply 142 having a d.c. section 144 and an a.c. section 146. The d.c. section 144 provides a switched positive 15 volt d.c. to a positive 5 volt d.c. regulator through conductor 148 located on circuit board 33 (FIG. 3). The alternating current section normally provides a sinusoidal 4 KHz signal used to energize the electroluminescent panel.

The d.c. section includes a conventional full wave rectifier 149 having two of its diagonals connected across the input transformer and the other two connected through filtering and regulator circuits 150 and 152 in a conventional manner to apply filtered potential of approximately a positive 15 volts to a conductor 154 and of a negative 15 volts to a conductor 156.

The conductor 154 is connected through normally open relay switch contacts 151A to one input of the a.c. section 146 through a conductor 158 and conductor 156 is connected through normally open relay switch contacts 151B to the a.c. section 146 through conductor 160. Conductor 154 is also electrically connected through an on-off switch to conductor 148 which is directly connected to the input of the positive 5 volt d.c. regulator. Conductor 148 is connected to the input of the positive 5 volt regulator and through relay coil 164 and a resistor 166.

To provide alternating potential for exciting the electroluminescent strips in the clipboard, the a.c. section 146 includes a Wein bridge oscillator 168 which is conventional in structure and which applies 4 KHz signals to the output transformer 170 through an amplification circuit 172. The secondary of the transformer 170 is electrically connected to each of conductors 40A–40C on one end and on the other end to conductors 44A–44C through the relay switches described above to provide the alternating current potential at selected times.

As can be understood from the foregoing description, the synchronizing clipboard of this invention provides several advantages such as: (1) it enables the user to coordinate notes with other data being recorded in a manner that enables a ready response to real time events and still permits accurate reconstruction; (2) it is relatively compact and easy to use such as by a nurse at an emergency station; (3) it provides unmistakable backup signals for events that might be overlooked in an emergency such as providing an audible alarm when the page must be changed; and (4) it is durable and relatively inexpensive.

Although a specific embodiment of the invention has been described with some particularity, many modifications and variations of the specific embodiment are possible without deviating from the invention. Therefore, it is to be understood that, within the scope of the appended claims, the invention may be practiced other than as specifically described.

What is claimed is:

1. A method of providing records of events during a cardiac arrest comprising the steps of:

generating timing signals at preset intervals, which intervals have a duration within the range of fifteen seconds and five minutes;

indicating sections of a chart, each having an area of at least 0.5 square centimeters in a time sequence corresponding to the time sequence of said timing signals;

recording observations on said chart at the indicated sections;

automatically sensing electrocardiographic data signals;

recording said automatically sensed electrocardiographic data signals as electrical signals with a predetermined frequency, which electrical signals have at least one characteristic which may change under some circumstances at unpredictable time periods which are greater than the period of said frequency of said signals but are less than the intervals between said timing signals;

the step of generating timing signals including generating timing signals having intervals greater than the time periods between changes in the characteristic of said electrical signals; and recording said timing signals with said automatically sensed electrocardiographic data signals, whereby the time said data was sensed is indicated and said sensed electrocardiographic data signals may be coordinated in time with said observations.

2. A method according to claim 1 which said step of indicating sections of a chart includes the step of indicating elongated sections forming columns, each corresponding to a time increment and having along their length other indications specifing different conditions.

3. A method ancillary to claim 2 in which said step of indicating sections of a chart includes the step of indicating sections having a length of at least three inches.

4. A method according to claim 3 including the steps of:

generating an audible signal after a predetermined number of timing signals have elapsed; and changing the chart after the audible signal is generated.

5. A method according to claim 4 in which the step of recording said automatically sensed electrocardiographic data signals includes the step of recording said automatically sensed electrocardiographic data signals on magnetic tape.

6. A method according to claim 5 in which:

the step of indicating includes the step of indicating columns having a length of approximately 8 inches; and the step of generating includes the step of generating timing signals at intervals of one minutes.

7. A method according to claim 2 including the steps of:

generating an audible signal after a predetermined number of timing signals have elapsed; and changing the chart after the audible signal is generated.

8. Apparatus comprising:

means for generating timing signals at preset intervals, which intervals have a duration within the range of fifteen seconds and five minutes;

a chart having sections, said sections having an area of at least 0.5 square centimeters;

means for indicating sections of said chart in a time sequence corresponding to the time sequence of said timing signals, whereby observations may be recorded on said chart at the time the sections are indicated;

electrocardiographic means for automatically sensing electrocardiographic data signals;

means for recording said automatically sensed electrocardiographic data signals as electrical signals with a predetermined frequency, which electrical signals have at least one characteristic which may change under some circumstances at unpredictable time periods which are greater than the period of said frequency of said signals but are less than the intervals between said timing signals;

the means for generating timing signals including the means for generating timing signals having intervals greater than the time periods between changes in the characteristic of said electrical signals; and means for recording said timing signals with said automatically sensed electrocardiographic data signals, whereby the time said data was sensed is indicated and said sensed data may be coordinated in time with said observations.

9. Apparatus according to claim 8 in which said sections are elongated columns each corresponding to a timing signal and having along their lengths rows corresponding to different conditions.

10. Apparatus according to claim 8 in which:

said chart includes a flow chart; and said means for indicating includes means for indicating sections of said flow chart.

11. Apparatus according to claim 10 in which said means for indicating includes means for illuminating sections of said flow chart.

12. Apparatus according to claim 11 further comprising means for recording said automatically sensed information.

13. Apparatus according to claim 12 further including means for periodically emitting an audible alarm.

14. Apparatus according to claim 13 in which said timing signals are electrical signals.

15. Apparatus according to claim 14 in which said means for indicating includes programmable means for indicating said sections at programmable periods.

16. Apparatus according to claim 15 in which said indicating means includes counters for determining said predetermined periods and electroluminescent lamp means for illuminating said flow charts.

17. Apparatus according to claim 16 in which said alarm means includes counter means for counting a predetermined number of timing pulses and audible means for sounding an alarm after a predetermined number of said timing pulses corresponding to the numbered sections on said flow chart, whereby a signal is given to change a flow chart.

18. Apparatus according to claim 17 in which said flow sheet includes columns for receiving observed data and said electroluminescent means includes means for exciting strips of said electroluminescent means beneath said columns in said predetermined sequence.

19. Apparatus according to claim 18 further including a plurality of lamps and means for illuminating the lamp indicating the number of predetermined periods that have elapsed, whereby the page of flow sheets is indicated.

20. Apparatus according to claim 19 in which said flow sheet includes a list of events for cardiac arrest.

21. Apparatus according to claim 20 in which said means for indicating forms a portion of a clipboard adapted to underlie flow sheets.

22. Apparatus according to claim 21 further including means for recording automatically sensed signals on magnetic tape.

* * * * *